US005465896A

United States Patent [19]
Allen et al.

[11] Patent Number: 5,465,896
[45] Date of Patent: Nov. 14, 1995

[54] LINEAR SURGICAL STAPLING INSTRUMENT

[75] Inventors: William J. Allen, Stratford; Jeffrey A. Stein, Milford; Paul DiCesare, Norwalk, all of Conn.; Paul Mulhauser; Doug Spranger, both of New York, N.Y.

[73] Assignee: United States Surgical Corporation, Norwalk, Conn.

[21] Appl. No.: 270,399

[22] Filed: Jul. 5, 1994

Related U.S. Application Data

[63] Continuation of Ser. No. 789,166, Nov. 7, 1991, abandoned.

[51] Int. Cl.$^6$ ................................................. A61B 17/072
[52] U.S. Cl. .............................. 227/176; 227/8; 227/19; 227/178; 227/180
[58] Field of Search .............................. 227/8, 19, 175, 227/176, 178, 180

[56] References Cited

U.S. PATENT DOCUMENTS

| | | |
|---|---|---|
| D. 283,733 | 5/1986 | Rawson et al. . |
| 2,174,219 | 9/1939 | Balma . |
| 2,246,647 | 6/1941 | Vancura . |
| 3,079,606 | 3/1963 | Bobrov et al. . |
| 3,490,675 | 1/1970 | Green et al. . |

(List continued on next page.)

FOREIGN PATENT DOCUMENTS

| | | |
|---|---|---|
| 5476486 | 9/1986 | Australia . |
| 5476586 | 9/1986 | Australia . |
| 0324638 | 7/1989 | European Pat. Off. . |
| 0373762 | 6/1990 | European Pat. Off. . |
| 0380025 | 8/1990 | European Pat. Off. . |
| 0489436 | 6/1992 | European Pat. Off. . |
| 206186 | 6/1908 | Germany . |
| 2070499 | 9/1981 | United Kingdom . |
| 8302247 | 7/1983 | WIPO . |

OTHER PUBLICATIONS

"Auto Suture® Premium Poly CM™–57 Disposable Surgical Stapler," printed 1986, reprinted 1990.
"Auto Suture® Poly CS™–57 Disposable Surgical Stapler", printed Jul. 1988.
"Auto Suture® Poly CS™–57 Disposable Loading Units with Lactomer® Absorbable Copolymer Staples", printed Jul. 1988.
"Disposable EEA Surgical Stapler and Curved Disposable EEA Surgical Stapler", Information Booklet, printed Jan. 1985.
Anderson et al., Surgical Stapling, "Thoraci, Vascular and Esophageal Procedures", pp. 1–101, 1988.

(List continued on next page.)

Primary Examiner—Rinaldi I. Rada

[57] ABSTRACT

A linear surgical stapling instrument includes a magazine for holding a plurality of undeformed surgical staples, and an upper jaw carrying the magazine and having opposed distal and proximal ends. An anvil is formed with staple-deforming pockets, and a lower jaw carries the anvil and has opposing distal and proximal ends respectively configured to mate with the distal and proximal ends of the upper jaw thereby to place the magazine and the anvil in confronting relation. A staple driver is carried in the upper jaw for driving staples held therein toward the anvil. Further, the upper and lower jaws are configured such that, when their respective distal and proximal ends are mated, a gap exists between the jaws in an intermediate region between their respective distal and proximal ends. Finally, a pivotably mounted clamp bar joins the upper and lower jaws and when actuated compresses them together in the intermediate region thereby to narrow the gap and to increase the clamping pressure between the magazine and the anvil. The instrument also includes a blocking system that prevents the jaws from being remated, once having been mated and having had staples in the magazine driven toward the anvil. Still further, the instrument includes a coupling device for coupling the jaws and clamp bar together when the staple driver is actuated.

10 Claims, 7 Drawing Sheets

U.S. PATENT DOCUMENTS

| | | |
|---|---|---|
| 3,494,533 | 2/1970 | Green et al. . |
| 3,499,591 | 3/1970 | Green . |
| 3,675,688 | 7/1972 | Bryan et al. . |
| 3,692,224 | 9/1972 | Astafiev et al. . |
| 3,735,762 | 5/1973 | Bryan et al. . |
| 3,795,034 | 3/1974 | Strekopytov et al. . |
| 3,844,289 | 10/1974 | Noiles . |
| 3,873,016 | 3/1975 | Fishbein . |
| 4,006,786 | 2/1977 | Speicher . |
| 4,086,926 | 5/1978 | Green et al. . |
| 4,108,306 | 8/1978 | Samuels et al. . |
| 4,202,479 | 5/1980 | Razgulov et al. . |
| 4,202,480 | 5/1980 | Annett . |
| 4,256,251 | 3/1981 | Moshofsky . |
| 4,296,881 | 10/1981 | Lee . |
| 4,304,236 | 12/1981 | Conta et al. . |
| 4,305,539 | 12/1981 | Korolkov et al. . |
| 4,319,576 | 3/1982 | Rothfuss . |
| 4,331,276 | 5/1982 | Bourque . |
| 4,349,028 | 9/1982 | Green . |
| 4,354,628 | 10/1982 | Green . |
| 4,383,634 | 5/1983 | Green . |
| 4,391,401 | 7/1983 | Moshofsky . |
| 4,415,112 | 11/1983 | Green . |
| 4,429,695 | 2/1984 | Green . |
| 4,442,964 | 4/1984 | Becht . |
| 4,473,077 | 9/1984 | Noiles et al. . |
| 4,480,640 | 11/1984 | Becht . |
| 4,500,025 | 2/1985 | Skwor . |
| 4,506,670 | 3/1985 | Crossley . |
| 4,508,253 | 4/1985 | Green . |
| 4,519,532 | 5/1985 | Foslien . |
| 4,520,817 | 6/1985 | Green . |
| 4,523,695 | 6/1985 | Braun et al. . |
| 4,527,724 | 7/1985 | Chow et al. . |
| 4,530,453 | 7/1985 | Green . |
| 4,540,110 | 9/1985 | Bent et al. . |
| 4,556,058 | 12/1985 | Green . |
| 4,568,009 | 2/1986 | Green . |
| 4,569,346 | 2/1986 | Poirier . |
| 4,576,165 | 3/1986 | Green et al. . |
| 4,576,167 | 3/1986 | Noiles . |
| 4,589,582 | 5/1986 | Bilotti . |
| 4,591,085 | 5/1986 | DiGiovanni . |
| 4,592,498 | 6/1986 | Braun et al. . |
| 4,597,517 | 7/1986 | Wagdy . |
| 4,605,004 | 8/1986 | DiGiovanni et al. . |
| 4,606,344 | 8/1986 | DiGiovanni ............................ 227/181 |
| 4,606,345 | 8/1986 | Dorband et al. . |
| 4,607,636 | 8/1986 | Kula et al. . |
| 4,608,981 | 9/1986 | Rothfuss et al. . |
| 4,612,933 | 9/1986 | Brinkerhoff et al. . |
| 4,617,928 | 10/1986 | Alfranca . |
| 4,640,745 | 3/1987 | Noiles ................... 227/19 X |
| 4,664,305 | 5/1987 | Blake, III et al. . |
| 4,665,916 | 5/1987 | Green . |
| 4,684,051 | 8/1987 | Akopov et al. . |
| 4,714,187 | 12/1987 | Green . |
| 4,715,520 | 12/1987 | Roehr, Jr. et al. . |
| 4,728,020 | 3/1988 | Green et al. . |
| 4,741,336 | 5/1988 | Failla et al. . |
| 4,807,628 | 2/1989 | Peters et al. . |
| 4,809,898 | 3/1989 | Gassner et al. . |
| 4,850,355 | 7/1989 | Brooks et al. . |
| 4,881,544 | 11/1989 | Green et al. . |
| 4,881,545 | 11/1989 | Isaacs et al. . |
| 4,915,100 | 4/1990 | Green . |
| 4,938,408 | 7/1990 | Bedi et al. ............................ 227/19 X |
| 4,941,623 | 7/1990 | Pruitt . |
| 4,955,959 | 9/1990 | Tompkins et al. . |
| 5,031,814 | 7/1991 | Tompkins et al. . |
| 5,071,052 | 12/1991 | Rodak et al. . |
| 5,100,042 | 3/1992 | Gravener et al. ...................... 227/176 |
| 5,106,008 | 4/1992 | Tompkins et al. . |
| 5,129,570 | 7/1992 | Schulze et al. . |

OTHER PUBLICATIONS

Brolin et al., Surgical Stapling, "Bariatric Procedures for Morbid Obesity", pp. 1–115, 1989.

Flickinger et al., Surgical Stapling, "Gastric and Small Bowel Procedures", pp. 1–145, 1988.

FIG_8A

FIG_8B

FIG_8C

LINEAR SURGICAL STAPLING INSTRUMENT

This is a continuation of U.S. application Ser. No. 07/789,166 filed on Nov. 7, 1991, now abandoned.

BACKGROUND OF THE INVENTION

1. Field of the Invention

The present invention relates to a linear anatomic surgical stapling instrument and a surgical staple magazine used therein. More particularly, the invention relates to a gastrointestinal anatomic stapling instrument, which is also known as a gastrointestinal anastomosis instrument or device, for suturing body organs and tissue and to such an instrument that includes a system for preventing its accidental reuse after a staple cartridge has initially been spent.

2. Description of the Prior Art

Historically, suturing of a surgical or other wound in organs and tissue has been done by hand. Conventional hand suturing techniques require a high degree of surgical skill. However, expertise in such techniques can vary widely from surgeon to surgeon, thereby resulting in widely varying quality in performance of the concluding steps of an operative procedure. In addition, even very skillful surgeons require a considerable amount of time to suture even relatively small wounds. Therefore, it is possible that an undesirable amount of blood may be lost during the suturing operation.

Accordingly, there has been an increasing tendency in recent years to use surgical staples to suture body organs and tissue after a medical procedure. Surgical staples have been particularly effective in suturing body organs and tissue such as the lung, as well as the esophagus, the stomach, the duodenum, and other body organs in the intestinal tract.

The advent of surgical stapling has provided several marked advantages over known hand suturing techniques. First, since one or more rows of surgical staples are inserted into tissue using a specially adapted instrument that is relatively simple to operate, near uniformity of the closure from one surgeon to the next results. In addition, all staples in the closure are usually inserted simultaneously or in rapid sequence across the entire wound. Therefore, the closure is made very quickly to minimize loss of blood.

The specially adapted instruments for inserting surgical staples are mechanically operated and may be known as anastomosis devices, such as the gastrointestinal anastomosis devices of the type to which this invention relates. In such devices, the staples are loaded in one or more elongated rows into a magazine or cartridge. The magazine is then mounted in the device, which includes a mechanism for pushing, or driving, the staples from the magazine through two or more sections of tissue toward a deforming anvil. At the conclusion of the driving operation, the legs of each staple are clamped or bent, by engagement with the anvil, to a closed configuration to complete the suture and join the tissue sections together.

Known gastrointestinal anastomosis stapling instruments usually include a pair of elongated jaws that are maneuvered to position the tissue to be sutured therebetween. The Jaws are then clamped tightly together. One of the Jaws supports the staple magazine with at least two laterally spaced rows of staples and cooperating staple drivers, and the other jaw supports an anvil with similar complementary rows of staple-forming pockets, each pair of which is aligned with one staple in the cartridge. A reciprocal slide is mounted with one jaw and when advanced therealong longitudinally actuates staple-driving cam surfaces to sequentially depress the staple drivers and drive the staples through the body tissue toward the anvil. Additionally, a knife blade may be advanced with the cam surfaces to slice the tissue between the two rows of deformed staples immediately following the staple deformation so that the adjacent sutured tissue sections can be separated.

Known surgical stapling instruments of the type described above can be made of reusable materials. However, most stapling instruments employed today are made of disposable materials so that they can be discarded after use on a single patient. The cost of manufacture is thereby lowered and problems associated with handling, repairing, reconditioning, and sterilizing of previously used instruments are eliminated. Specifically, the risk of spreading infection from patient to patient due to improperly sterilized instruments is thus reduced and the surgeon can be confident that each fresh instrument he or she picks up is sharp and in good working order.

While stapling instruments are, therefore, generally made to be disposed of after use for a given patient, it is also known to use one stapling instrument more than one time during an operation on one patient. Thus such instruments are usually designed to be reloaded by replacing a spent staple magazine with a full one.

As may thus be expected, linear stapling instruments provide many benefits, such as those described above. However, they also have certain drawbacks. For one, they have difficulty maintaining a constant tissue gap between the jaws after the jaws are clamped together, and a high constant clamping pressure on tissue between the jaws. More particularly, forces created when the staples are driven through the tissue into the anvil tend to urge the jaws apart and, if not controlled, produce unevenly deformed staples and an unsatisfactory suture.

U.S. Pat. Nos. 4,633,861 (Chow, et al.) and 4,633,874 (Chow, et al.) relate to stapling instrument designs that attempt to counteract such forces by providing a cam mechanism for urging the jaws apart at an opposite end from where the tissue is clamped. The cam mechanism is located in the handle of one of the jaws and is actuated by the sliding motion of a staple-driving pusher bar or slide. Alternative stapling instrument designs are described in U.S. Pat. Nos. 4,429,695 (Green, et al.) and 4,520,817 (Green) and include sliding shoes that project into complementary slots in the upper and the lower jaws to secure the jaws together in opposition to forces otherwise tending to urge the jaws apart. However, these mechanisms for counteracting the forces tending to separate the jaws when the stapling instrument is actuated are complex. Moreover, they require relatively large effort to activate at the beginning of the staple-driving operation. Such effort may be physically difficult for some surgeons to generate and may cause the instrument to jerk abruptly upon such actuation while engaged on the body tissue.

Another drawback of many known linear stapling instruments is that they lack adequate mechanisms to prevent exposure to the knife blade when the jaws are open and to prevent a surgeon from mistakenly attempting to use the instrument when it is loaded with a spent staple magazine. For example, if a surgeon performs a procedure with a stapling instrument having a spent staple magazine, no suture will in fact be formed despite the surgeon's expectations. Therefore, when he removes the instrument from the tissue, the wound will not be closed and may bleed.

Some attempts have been made to address these latter difficulties. For example, U.S. Pat. No. 4,892,244 (Fox) relates to surgical staple magazines having various safety features designed to prevent the reloading or refiring of the magazines once spent. However, the designs disclosed in that patent do not prevent the jaws of the stapling instrument from being closed on tissue to be sutured while it contains a spent staple magazine that has not been replaced with a loaded one. Therefore, the surgeon may reclamp the instrument and actuate it, expecting a proper suture to have been formed when it has not.

Accordingly, further advances and improvements in linear surgical stapling instruments are needed.

SUMMARY OF THE INVENTION

Accordingly, it is an object of the present invention to provide a linear surgical stapling instrument having a simple mechanism for maintaining a high and constant tissue-clamping force between the jaws.

It is another object of the present invention to provide a linear surgical stapling instrument having a safety feature that prevents exposure of the knife blade when the instrument is assembled and the blade is in an advanced cutting position.

It is yet another object of the present invention to provide a surgical staple magazine having a safety feature that prevents reclosing of the jaws of the instrument after it has once been used and the staples in the magazine have been spent.

It is still another object of the present invention to provide a method for optimally configuring the staple driving elements and thereby reduce the effort required for the surgeon to operate the instrument.

Another object of the present invention is to provide an ergonomically improved configuration for a linear stapling instrument that is thereby easy to use.

These and other objects are achieved by the present invention, which in a preferred embodiment is a linear surgical stapling instrument including a magazine for holding a plurality of undeformed surgical staples, and an upper jaw carrying the magazine and having opposed distal and proximal ends. An anvil is formed with staple-deforming pockets, and a lower Jaw carries the anvil and has opposing distal and proximal ends respectively configured to mate with the distal and proximal ends of the upper jaw thereby to place the magazine and the anvil in confronting relation. A staple driver is carried in the upper jaw for driving staples held therein toward the anvil. Further, the upper and lower jaws are configured such that, when their respective distal and proximal ends are mated, a gap exists between the jaws in an intermediate region between their respective distal and proximal ends. Finally, a pivotably mounted clamp bar joins the upper and lower jaws and when actuated compresses them together in the intermediate region thereby to narrow the gap and to increase the clamping pressure between the magazine and the anvil.

The clamping mechanism in accordance with the present invention thus provides constant high clamping forces between the upper and lower jaws to ensure reliable suturing operation.

In accordance with another aspect of the present invention, the preferred embodiment is a linear surgical stapling instrument that comprises a magazine for holding a plurality of undeformed surgical staples in a linear row, and an upper Jaw carrying the magazine. An anvil formed with staple-deforming pockets therein is carried in a lower jaw. The upper and lower jaws are configured to mate with each other with the magazine and the anvil in confronting relation. A staple driver actuator is mounted in the upper jaw for movement from one end thereof toward the magazine to operate staple drivers and drive the staples from the magazine toward the anvil. The actuator includes a coupling structure that couples both the upper and lower jaws together when the actuator is moved toward the magazine.

Accordingly, the present invention also provides a mechanism whereby the jaws are prevented from opening once clamped about tissue to be sutured and the instrument is actuated to drive the staples. In this way a knife blade moved with the staple driver is shielded when in an advanced position.

In accordance with yet another aspect of the subject invention, a preferred embodiment is a linear surgical stapling instrument comprising a magazine for holding a plurality of undeformed surgical staples, and an upper jaw carrying the magazine. An anvil, formed with staple-deforming pockets therein, is carried in a lower jaw. The upper and lower jaws are configured removably to mate with each other with the anvil and the magazine in confronting relation. A staple driver is mounted in the upper jaw for driving staples held in the magazine toward the anvil. Finally, the lower jaw, and preferably the magazine, is provided with a blocking member for preventing the upper and lower jaws from being remated with each other after having been once mated and having the staples in the magazine driven toward the anvil to complete the suture.

Thus the present invention provides a mechanism whereby, once the suture has been made and the upper and lower jaws have been opened to release the sutured tissue, the instrument cannot be reclamped to make a new tissue suture until the spent staple magazine is replaced.

In another aspect, the present invention includes offset and angled advancers that operate staple drivers in at least two rows to drive staples to form the suture. The offset of the advancers and the angle of their staple driving surfaces are determined to minimize peak operating effort required of the surgeon to operate the instrument and thereby complete the suture.

Toward the same aim, the linear stapling instrument of the present invention is formed with grips at carefully selected locations to properly and reliably position the surgeon's hands and fingers during operation of the instrument.

These and other objects, aspects, features, and advantages of the present invention will become apparent from the following detailed description of the preferred embodiment taken in conjunction with the accompanying drawings.

DESCRIPTION OF THE PREFERRED EMBODIMENTS

Figure 1:
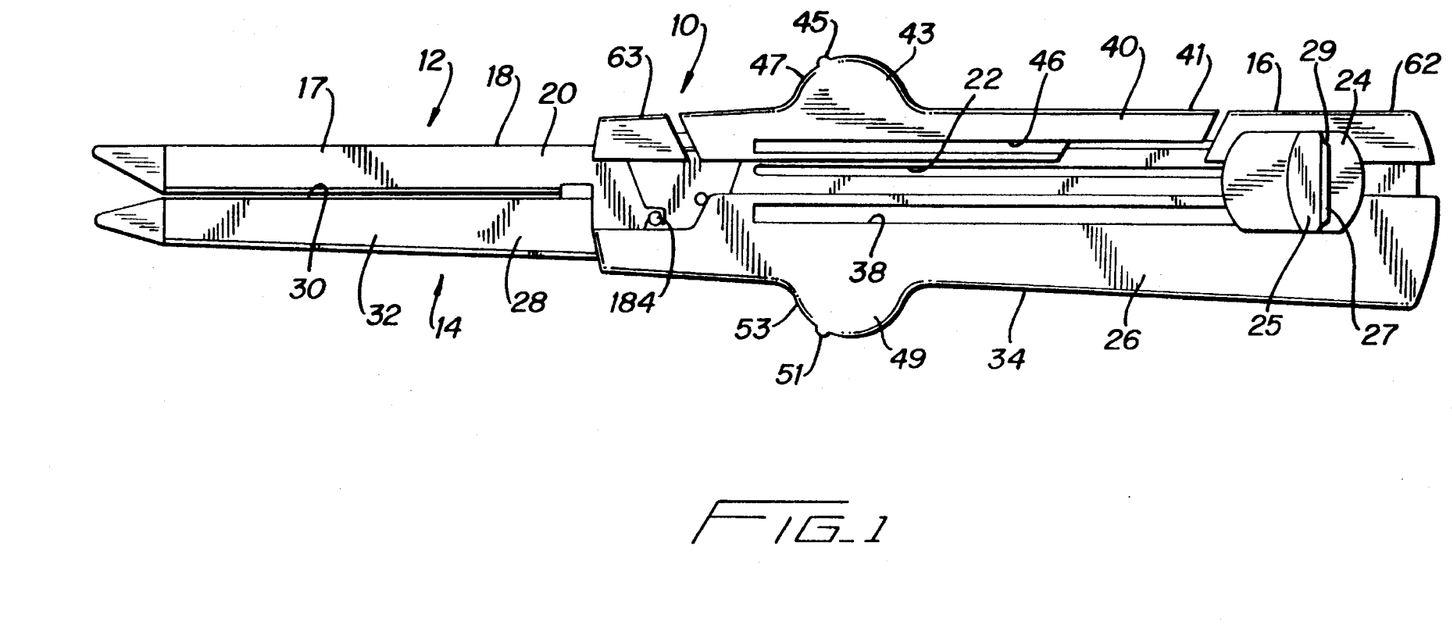
FIG. 1 is side elevational view of the linear surgical stapling instrument in accordance with the preferred embodiment of the present invention.
Figure 2:
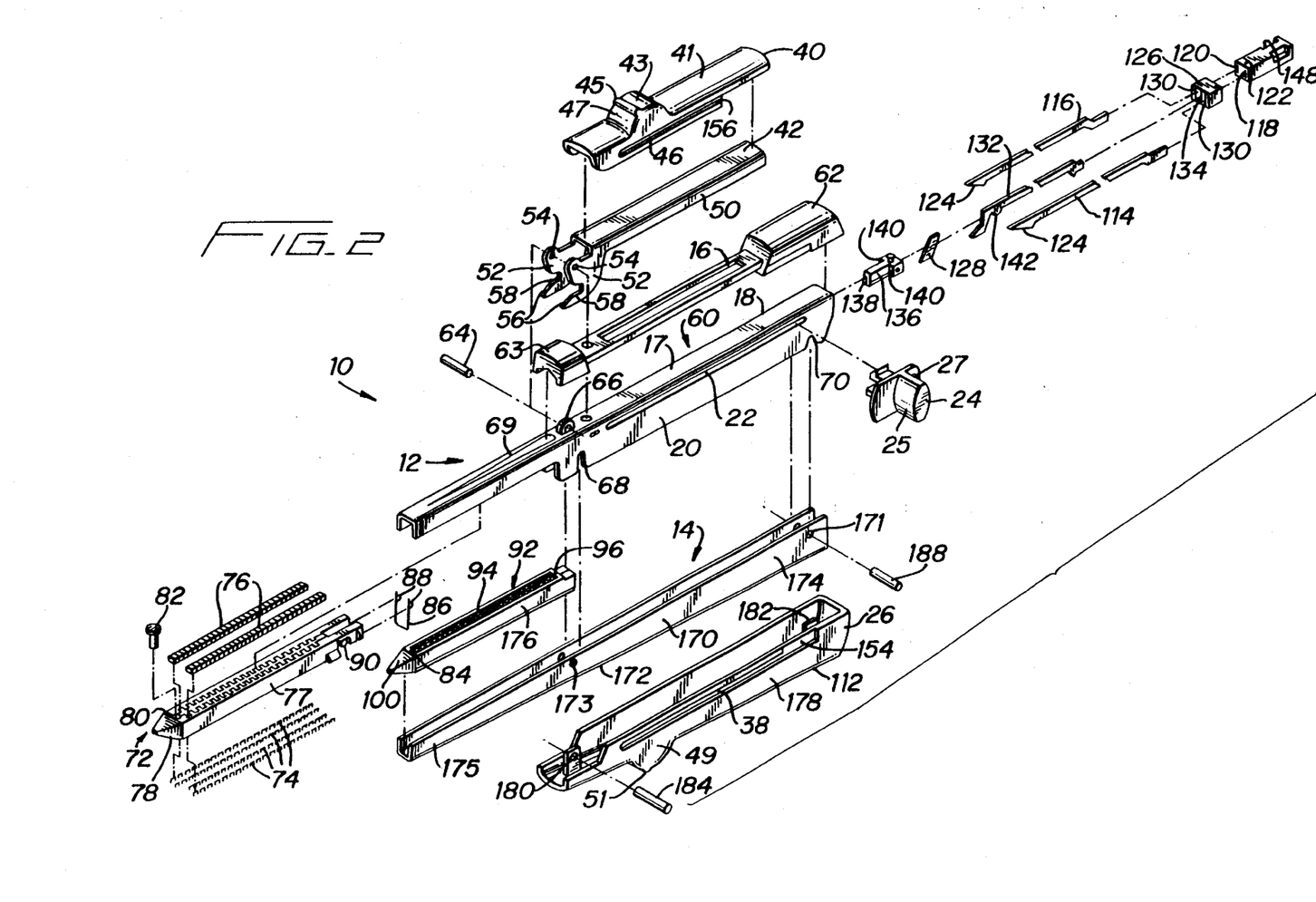
FIG. 2 is an exploded perspective view of the linear surgical stapling instrument in accordance with the preferred embodiment of the present invention.

The major components of the linear surgical stapling instrument, generally indicated at 10, in accordance with the preferred embodiments of the subject invention are shown in FIGS. 1 and 2. That instrument includes an upper elongated jaw member 12 and a lower elongated jaw member 14 for gripping therebetween tissue to be sutured. The upper jaw member 12 comprises a top housing 16 which partially encloses an elongated top beam 17 as best seen in FIG. 2. The top beam has an inverted U-shape defined by a top wall 18 and side walls 20 that can be formed of heavy gauge metal. The top beam has an elongated slot 22 in one side wall 20 along which a manually manipulatable actuator 24 may slide as will be described in more detail below. The lower jaw member 14 includes a bottom housing 26 that partially encloses a bottom beam 170, which similarly may be formed of heavy gauge metal, having a U-shaped cross section defined by a bottom wall 172 and opposing side walls 174. The bottom housing 26 has a U-shaped cross section defined by a bottom wall 34 and side walls 178. One such side wall 178 of the bottom housing 26 includes an elongated groove or channel 38 for receiving a portion of the actuator 24 in a manner described in greater detail below. A clamp housing 40 is secured over a clamp bar 42, and the assembly is pivotably mounted on the top beam 17 to clamp the upper and lower jaw members together by gripping a front clamp pin 184 secured in an intermediate region of the bottom beam 170 between its distal and proximal ends. The clamp housing 40 also includes an elongated groove or channel 46 formed in one side for receiving another portion of the actuator 24, again as will be described further below.

The respective housings 16, 26, and 40 may be made of molded plastic.

Referring now more specifically to FIG. 2, the components of the first embodiment of the linear surgical stapling instrument of the subject invention, including the staple magazine, are shown in detail. Beginning at the top of the Figure, it will be seen that the clamp housing 40 has a top surface 41 that is contoured to fit a surgeon's hand comfortably and that has a enlarged finger grip 43 at a forward end, provided with a non-slip surface. The finger grip is formed with a laterally extending ridge 45 at its forward end that tends to hold one of a surgeon's fingers on the forward surface 47 of the grip during operation of the device. It will be understood that the bottom housing 26 also is formed with a finger grip 49, having a laterally extending ridge 51 that together complement the grip 43 and ridge 45 on the clamp housing 40, as seen in FIG. 1. Again the ridge 51 tends to hold another of the surgeon's fingers on the forward surface 53 of the grip 49. The actuator 24 has a thumb tab 25 having a ridge 27 on its rear surface 29 at its outermost edge. This ridge 27 similarly aids in locating the thumb of the surgeon's opposite hand to actuate the device as will the described in greater detail below.

The clamp housing can be snap-fit onto an elongated handle 50 defining a major portion of the clamp bar 42, which may also be formed of heavy gauge metal. The elongated groove 46 runs longitudinally along the side of the clamp housing.

The clamp bar 42 has spaced parallel hooks 52 at the forward end of the handle 50 formed with pivot pin receiving holes 54 and complementary cam surfaces 56 and clamp pin receiving slots 58 to which the cam surfaces 56 lead.

The top housing 16 provides a cover for a handle portion 60 of the top beam 17. The top housing is therefore shaped to have a palm rest portion 62 and a front upper jaw cover 63 that together complement the clamp housing 40 to provide a smooth upper surface when the clamp bar-housing assembly is closed, as best seen in FIG. 1.

The clamp bar 42 and its housing 40 are mounted for pivoted movement on the top beam 17 by a pivot pin 64 that extends through a lance 66 punched from the top wall of the top beam 17 and is received in the holes 54 in the clamp bar hooks 52. The lance 66 has a narrow width relative to that of the top beam and preferably is less than one-half the width of the top beam. In this way, the rigidity of the top beam 17 at the location where high compression bending forces are applied, as will be described further below, is not undesirably compromised.

In addition, as discussed above, the elongated slot 22 in the top beam 17 extends substantially along the entire handle portion. An identical symmetrically located elongated slot, not shown, is formed in the opposite side wall 20 of the top beam 17 from the slot 22. That unseen slot provides a symmetrically formed top beam and reduces top beam torsion therein during operation.

A stiffening rib 69 may also be provided by being pressed in the top wall 18 to add strength to the top beam 17 in the region of its distal end.

The side walls 20 of the top beam 17 are formed with clamp pin notches 68, in the intermediate region between the distal and proximal ends, and rear pin notches 70 in the region of the proximal ends. Both the clamp pin and rear pin notches having widely chamfered openings and respectively receive the clamp pin 184 and a rear pin 188 also carried in the bottom beam 18, as described further below. Both of the clamp and rear pins project beyond the side walls 32 of the bottom beam 28. It will also be appreciated that the side walls 20 of the top beam are spaced by slightly more than the distance between the outer surfaces of the side walls 32 of the bottom beam. Therefore, the top beam can be received over the bottom beam with the clamp and rear pins and notches fit together as described. Accordingly, the clamp pin notches and clamp pin and rear pin notches and rear pin collectively cooperate precisely to position the top and bottom beams with respect to each other for the stapling operation.

The inverted U-shaped channel defined by the top beam receives a disposable staple magazine or cartridge 72, having a housing 78 preferably loaded with four rows of staples 74 and two rows of staple drivers 76. The staple drivers 76 can be driven downwardly in turn sequentially to form the staples 74 in the longitudinal rows to define the suture.

A blocking member in the form of a safety spring 86 is mounted at the other end of the magazine housing 78. The safety spring has a pair of coils 88 each of which embraces a knob 90 extending from opposite sides 77 of the magazine housing 78. The spring has a loop that usually rests in a retracted position against the housing, but is released by the sliding action of the actuator 24 and its associated components as will be discussed in detail below.

The stapling instrument in accordance with preferred embodiment of the subject invention is designed specifically for use with malleable plastic or polymeric staples. The polymeric staples that are used in conjunction with the subject invention are formed in substantially the same manner as metal staples and are the subject of U.S. patent applications Ser. Nos. 07/548,802 and 07/548,803, both filed Jul. 6, 1990, which are incorporated herein by reference.

Thus, more particularly, the lower jaw member 14 includes the bottom beam 170 having a U-shaped cross section defined by a bottom wall 172 and two side walls 174. The bottom beam 170 has a tapered shape with a pair of rear pin holes 171 being offset from a pair of clamp pin holes 173. The distal end of the bottom beam defines an anvil supporting extension 175 shaped to receive a removable plastic anvil 176. The anvil has a surface 92 formed with linear rows of pairs of staple forming pockets for deforming staples driven theretoward. The anvil surface also includes a longitudinal slot 96 dividing the rows of pockets 94. The slot 96 has a floor or ramp, not shown, that slopes at a slight angle downwardly toward the nose 100 of the anvil.

The plastic anvil 176 can be made of conventional injection molded plastic material and is designed to bend plastic staples as described above. However, this embodiment can be used with both plastic and metal staples simply by mounting a plastic anvil or a metal anvil in the bottom beam 170 as appropriate.

In accordance with the subject invention, the magazine housing 78 has an opening 80 in one end through which a gap pin 82 extends. The gap pin is received in a small depression or socket 84 in the distal end of the anvil 176 beam 28 of the lower jaw member 14 to align the upper and lower jaw members when mated together and to maintain a minimum gap width between the distal ends of the jaw members.

As noted above, the width of the bottom beam 178 is such that it fits within side walls 178 of the proximal end of the bottom housing 26. An upstanding clamp pin anchor 180 and a rear pin anchor 182 extend from the bottom housing through slots, not shown, in the bottom beam 170. A clamp pin 184 extends through the clamp pin holes 173 and the clamp pin anchor 180 and a rear pin 188 extends through the rear pin holes 171 to secure the bottom beam in the bottom housing.

The extended groove 38 in the bottom housing 26 runs longitudinally along the handle portion thereof.

Finally, the lower surface 112 of the bottom housing 26 is also contoured to be comfortably gripped by the surgeon, and, as noted, has the enlarged finger grip 49 and laterally extending ridge 51, complementary to the finger grip 43 and ridge 45 on the clamp housing 40.

As can be seen in FIG. 2, the bottom beam 170 is tapered such that the side walls 178 at their proximal ends are wider than at their distal ends. In this way, the bottom wall 30 slopes slightly upwardly from the proximal end to the distal end of the beam. In addition, the rear pin 188 is offset from the clamp pin 184 by being at a higher vertical position relative to the top of the bottom beam 170. Thus the rear pin 188 is elevated with respect to the clamp pin 184 or is closer to the top edge of the top beam than is the clamp pin. The rear pin notches are configured in a complementary manner thereby to slightly raise the proximal end of the top beam 17 relative to the bottom beam 170 when the upper and lower jaw members are mated together.

More particularly, when the upper and lower jaw members 12 and 14 are mated together with their distal ends abutting each other through the medium of the gap pin 82 and pin socket 84, the proximal ends of the top and bottom beams are spaced by a gap because of the location of the rear pin and the depth of the rear pin notches. However, when the clamp bar 42 is pivoted from its open position to its closed position with the cam surfaces underriding the clamp pin 184, the intermediate region of the top beam is drawn or compressed toward the same region of the bottom beam until the clamp pin 184 resides in the clamp pin receiving slots 58 of the clamp bar hooks 52, as shown in FIG. 1. The clamp pin notches 68 have sufficient depth relative to the location of the clamp pin to accommodate this movement. The net effect of this mechanism then is to provide a downward compression force between the distal ends of the top and bottom beams 17 and 170 between their intermediate regions. This compression force is created when the clamp bar is fully closed and acts to resist the tendency of the upper and lower jaw members to separate when the staples are being formed. In addition, the configuration of the gap pin 82 in the upper jaw member cooperating with the socket 84 in the anvil 176 carried in the lower jaw, and of the clamp pin 44 in the lower jaw member cooperating with the clamp pin notches 68 in the upper jaw member ensure that the compression force results in a desired uniform tissue gap between the jaw members between their distal ends and intermediate region.

Of course, structures other than the clamp bar described above for creating the compression force between the intermediate regions of the top and bottom beams and consequently between the distal ends of the beams when the clamp bar is closed are within the scope of this invention. Further, other structures may be contemplated for spacing the proximal ends of the beams when the distal ends thereof abut each other so that compression between the beams in the intermediate region produces high clamping pressure between the distal ends of the jaw members.

Accordingly, it will be understood that the clamping mechanism of the present invention produces in high compression forces between the upper and lower jaw members, and tissue residing therebetween, at a constant tissue gap that maybe be uniform between the distal ends and intermediate region of the jaw members. It has been found that pressure between the distal ends of the jaw members in the range from about 40 to about 60 pounds is optimal. This pressure can, of course, be selected by selecting the particular locations and configurations of the gap pin and associated socket the clamp pin, clamp pin notches, and clamp bar hooks, and the rear pin and rear pin notches.

Further, this compression force is created before the instrument is actuated to insert the surgical staples. Therefore, the actuator 24 can be smoothly operated with relative low uniform effort to create the suture.

FIG. 2 also shows the elements comprising the actuator 24 and its associated mechanism for driving the staples 74 in the magazine 72 toward the anvil surface 92 and for coupling the upper and lower jaw members, as well as the clamp bar, together all in accordance with the present invention. More particularly, the actuator mechanism includes a left advancer 114 and a right advancer 116, for actuating the staple drivers 76 in the staple magazine, secured in slots 118 and 120 in an actuator mount 122. The right and left advancers each include a cam surface 124 for contacting the staple drivers and forcing them downwardly when the advancers are moved from right to left as shown in the Figure. An optional knife mount 126 may also be operated with the actuator mechanism and is used in conjunction with a cutting blade 128. The knife mount 126 includes outer slots 130 through which the right and left advancers extend before being secured in the actuator mount 122. A knife advancer 132 is secured in a middle slot 134 in the knife mount 126. The angled cutting blade 128, which may be canted upwardly and backwardly, is attached to the lead end of cutting blade support member or knife advancer 132. A guide 136 is secured at an intermediate position in the top beam and provides a guiding slot 138 for guiding the knife advancer 132 and guiding slots 140 for guiding the right and left advancers 116 and 114 through the top beam. The knife advancer 132 includes a trip structure or bump 142 for actuating the safety spring as will be discussed below.

Figure 3:
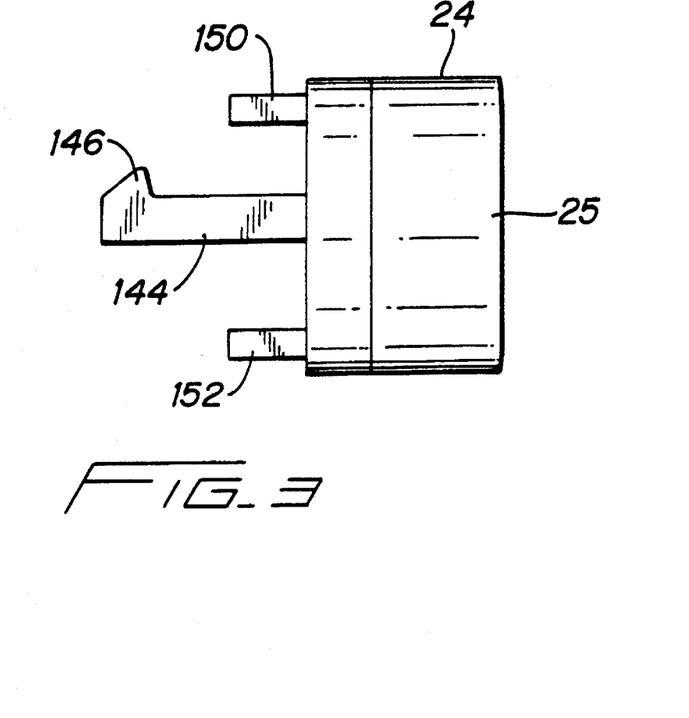
FIG. 3 is a front elevational view of the actuator for the staple driver carried in the upper jaw of the linear surgical stapling instrument in accordance with the preferred embodiment.

The actuator 24 is mounted with the upper jaw member and is connected to the actuator mount 122 to drive all of the advancers as follows:

Referring more particularly to FIGS. 2 and 3, the actuator 24 includes a driving finger 144 that fits through the slot 22 in the top beam 17 and has an upturned lip 146 that is snap-fit behind a connecting bar 148 in the actuator mount 126. An upper coupling finger 150, shown in FIG. 3 but which cannot be seen in FIG. 2 and which is a channel follower, is directly aligned with an entrance 156 at the proximal end of the groove 46 in the clamp housing 40 for sliding movement therein when the clamp housing is closed and when the actuator 24 is advanced, or fired, from right to left. Similarly, a lower coupling finger 152, which also cannot be seen in FIG. 2 and also is a channel follower, is positioned below the driving finger 144 and is positioned to be received in and slide in the channel 38 of the bottom housing when upper and lower jaw members are clamped together and the actuator 24 is fired. An entry way 154 is formed at the proximal end of the channel 38 to receive the lower coupling finger 152 when the jaw members are closed, thereby to align the finger 152 with the elongate run of the channel 38. In this way, when the actuator is in the ready-to-fire position, as shown in FIG. 1, the top beam 17 is free to pivot about rear pin 188. However, when the actuator is fired and the cutting blade 128 and cam surfaces 124 are advanced forwardly by the actuator and associated advancers, the lower coupling finger 152 will be received within the channel 38 and the upper coupling finger 150 will be received within groove 46, thereby preventing the jaw members from being separated and the clamp bar from being opened.

Thus, the present invention incorporates an important safety feature that prevents the operator of the stapling instrument and the patient from being exposed to the advanced cutting blade 128.

The present invention also contemplates a method by which the surgical stapling instrument can be configured so that staple forming forces are optimized. In this way, the effort required of the surgeon to advance the actuator can be minimized.

Figure 4:
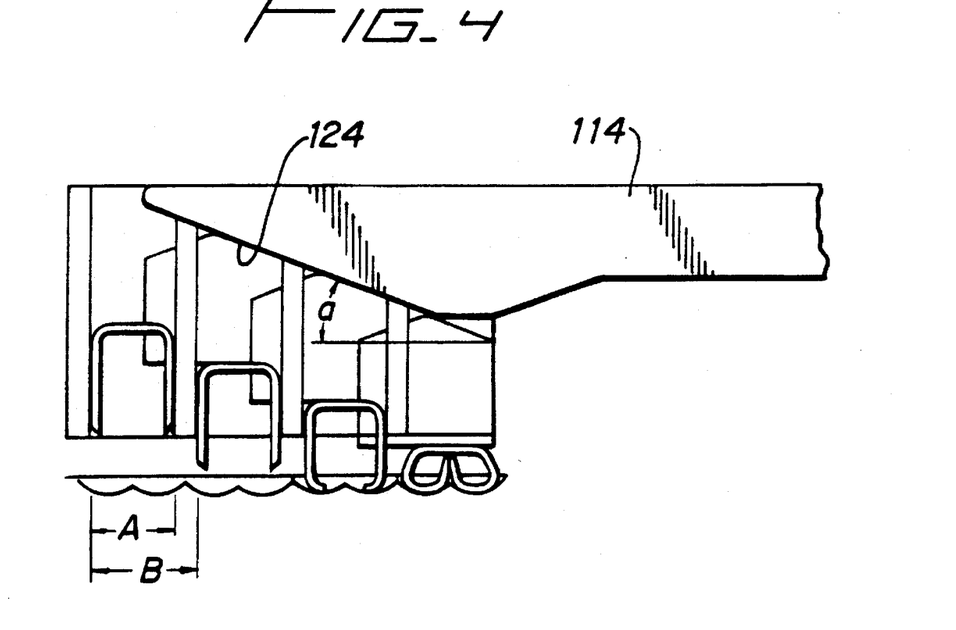
FIG. 4 is a detailed internal view of a staple driving cam surface on an advancer and a similar head on a number of staple drivers, the configuration of which are considered in optimizing staple driving forces.

It is known that advancers such as 114 and 116 may be mounted so that their respective cam surfaces 124 offset, as shown in FIG. 2. In this way, staples in opposing rows in the magazine 72 are not driven simultaneously, but alternatingly, thereby to reduce the operating effort. This relationship is shown, for example, in U.S. Pat. No. 4,429,695. The present invention seeks to enhance the benefit of such offset mounting by optimizing it in cooperation with the advancer driving wedge angle. As shown more specifically in FIG. 4, each staple driver 76 in the magazine 72 has a driving head 73 formed at an angle $\alpha$ to the horizontal. The cam surfaces 124 of the advancers 114 and 116 are formed at a similar angle $\alpha$. The forming forces exerted by the advancers on the stapler through the drivers are non-linear. That is, a first forming force curve as a function of time rises to a peak when the staple points hit the anvil and rapidly drop as the legs buckle, as depicted in FIG. 4. The force curve rises again to a second lesser peak as the legs are forced inwardly again as depicted in FIG. 4. Thus the cam surface-driving head angle $\alpha$ is optimized for the force curve that exhibits the lowest peak force as a function of time.

A similar second force curve may be determined dependent on the offset of the advancer cam surfaces 124 relative to the back span A of each staple and the pitch B between adjacent staples. The offset is thus optimized for the force curve that again exhibits the lowest peak force as a function of time.

Accordingly, the present invention contemplates providing an advancer cam surface angle $\alpha$ and adjacent advancer cam surface offset represented by the respective first and second force curves, the sum of which results in the lowest peak force.

For example, it has been found that for metal staples having a 3 mm backspan A, shown in FIG. 4, spaced at a 4 mm pitch B, driving forces are optimized at a cam surface angle $\alpha$ equal to 20° and an advancer offset equal to 2 mm.

Figure 5:
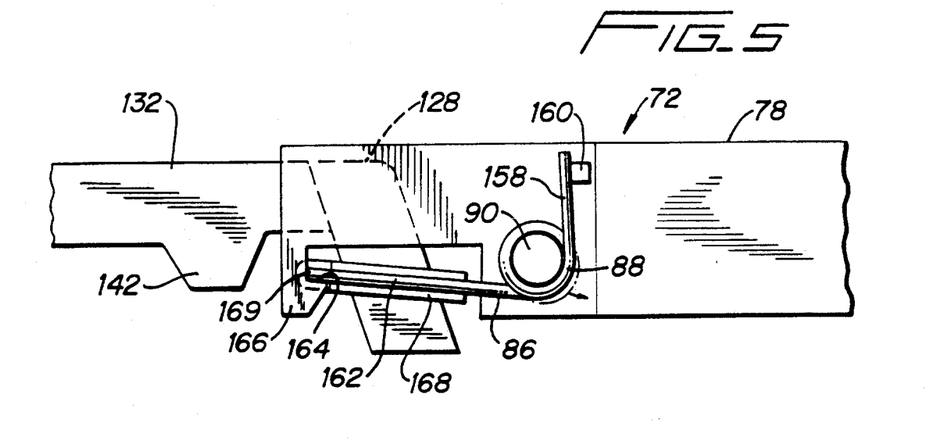
FIGS. 5 and 6 are a partial side elevational view and a partial top plan view, respectively, of the housing for the staple magazine in accordance with the preferred embodiment of the present invention.
Figure 6:
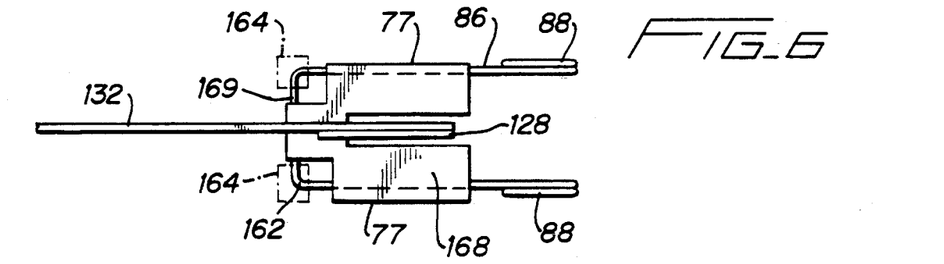
Figure 7:
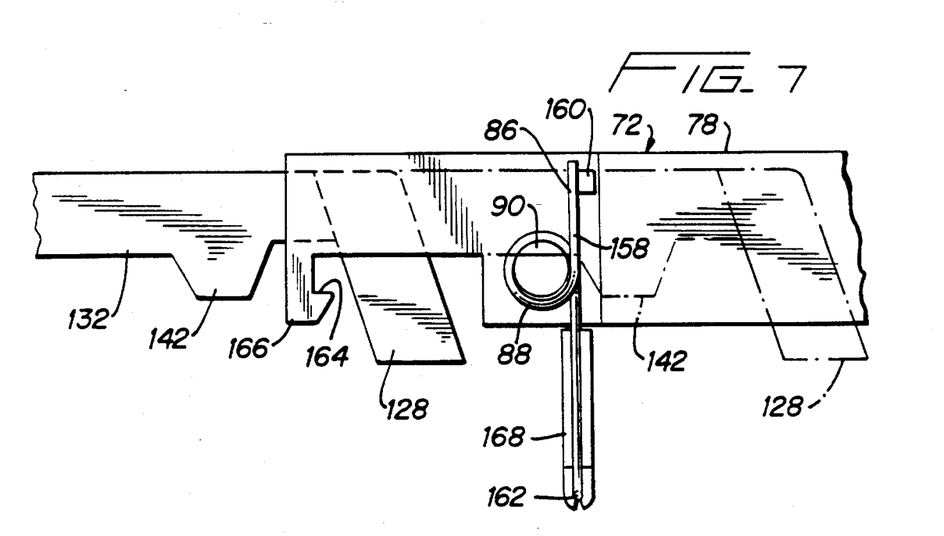
FIG. 7 is a partial side elevational view of the staple magazine shown in FIGS. 5 and 6, depicting a safety blocking member in the fully deployed position.

The mechanism for preventing reuse of the linear surgical stapling instrument in accordance with the present invention after it has been fired but before the spent staple magazine has been replaced, will now be described with reference to FIGS. 5, 6 and 7. For simplicity, these figures, which are reversed from FIGS. 1 and 2, only show the relationship between the staple magazine 72 and the knife advancer 132. FIG. 5 shows the knife advancer 132, trip bump 142 and cutting blade 128 of the stapling instrument, and the proximal end of the staple magazine 72. The cutting blade is shown in its ready-to-fire position, straddled by the sides 77 of the staple magazine housing 78 and the safety spring 86. As noted above, the safety spring 86 has a central loop portion having coils 88 mounted on knobs 90 of the staple magazine housing 78 with a first depending leg portion or extension 158 maintained in a stationary position against stop 160 and a second depending leg portion or loop extension 162 temporarily held in a non-blocking position by a securing mechanism having projecting ridges 164 on a latch 166. The spring force of the safety spring biases the loop extension to rotate in a counterclockwise direction. FIG. 6 is a top view of the staple cartridge and illustrates an optional visible flag 168 that can be attached to the safety spring 86.

Referring now to FIG. 5, when the knife advancer is moved forwardly from left to right in this view by sliding action of the actuator 24, the trip bump 142 pushes the second loop extension 162 toward the knobs 90 to bow the back 169 of the loop and release the second loop extension 162 from the projecting ridges 164. At this point, the unlatched safety spring is actuated but retains its L-shape because the second loop extension hits the top wall 30 of the bottom beam 28 when the upper and lower jaw members are closed together. However, when the stapling operation is completed and the upper and lower Jaw members are opened, the safety spring will fully deploy to the blocking position shown in FIG. 7. The safety spring in the fully deployed position thus will prevent the jaw members from being reclosed, until the spent staple magazine is replaced with a loaded magazine. In this way, the jaw members cannot be inadvertently reclosed on tissue to be sutured while the spent cartridge remains in the stapling instrument.

Figure 8A:
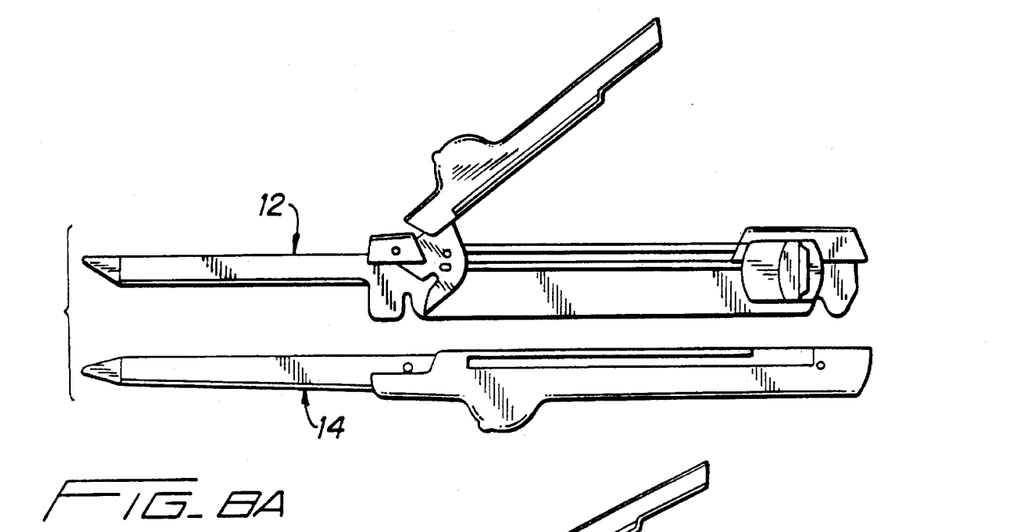
FIGS. 8A through 8I are a set of side elevational views showing the sequence of operations of the linear surgical stapling instrument in accordance with the preferred embodiments of the present invention.
Figure 8B:
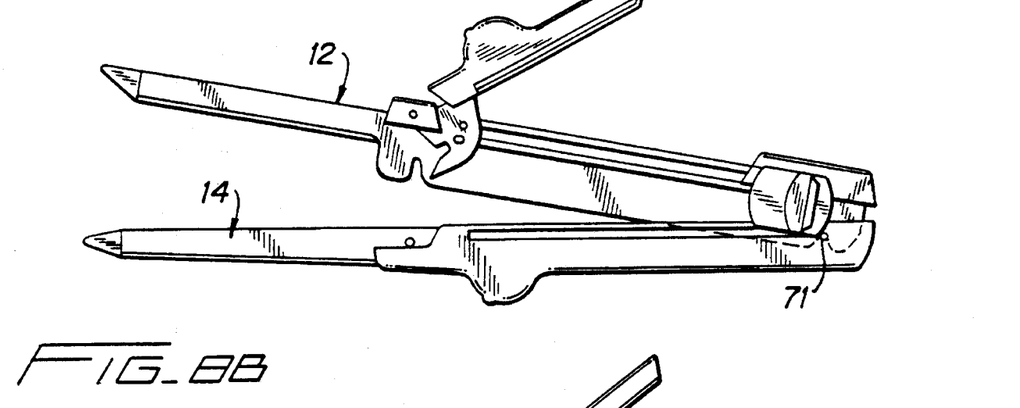

The sequence of operation of the linear surgical stapling instrument in accordance with the preferred embodiments of the present invention is shown in FIGS. 8A through 8I. FIG. 8A shows the upper and lower jaw members 12 and 14 unmated from each other, and FIG. 8B shows the upper jaw member pivoted about the rear pin 188 of the second jaw member whereby the jaw members are partially mated. In both positions shown in FIGS. 8A and 8B, the upper and lower jaw members may be maneuvered to position the body organ or tissue to be sutured therebetween.

Figure 8C:
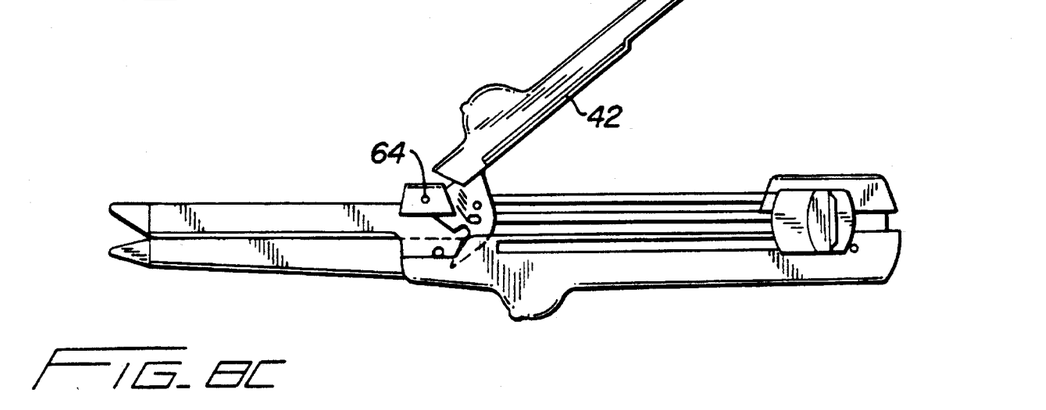
Figure 8D:
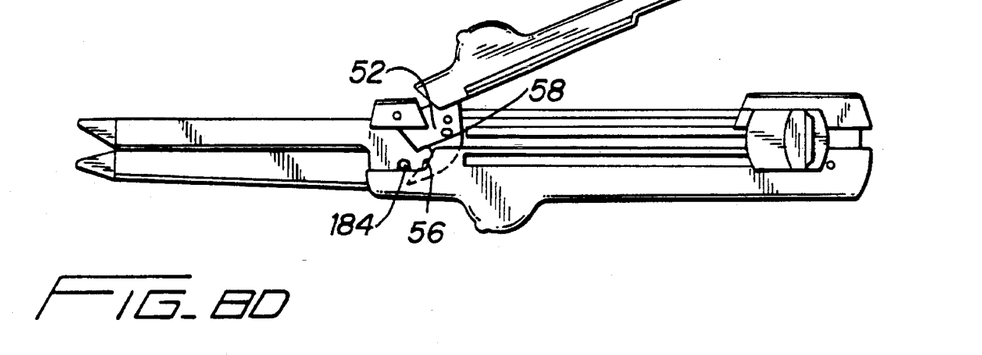
Figure 8E:
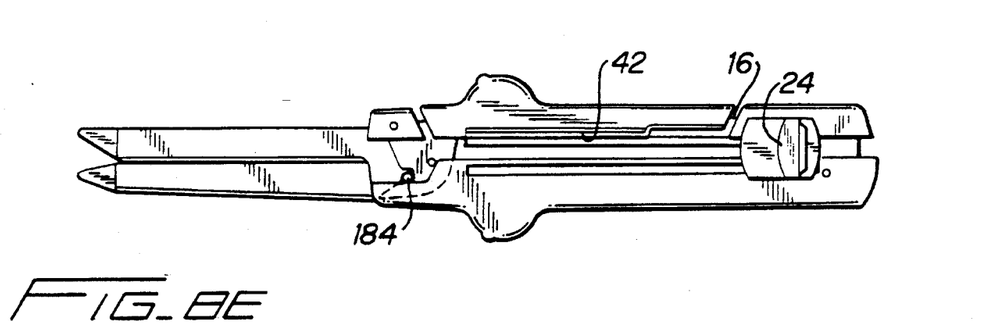

FIGS. 8C to 8E show the clamping of the upper and lower jaw members together. With the upper and lower jaw members in a closed position, clamping is initiated by rotating the clamp bar 42 clockwise about the pivot pin 64. FIG. 8D shows the cam surfaces 56 of the clamp bar hooks 52 underriding the clamp pin 184 anchored in the bottom housing 178. The stapling device is fully closed when the clamp bar is positioned flush against the top housing 16 and the clamp pin 184 is resting in the clamp pin receiving slots 58 of the hooks 52. In this attitude, as shown in FIG. 8E, the actuator 24 is in the ready-to-fire position.

Figure 8F:
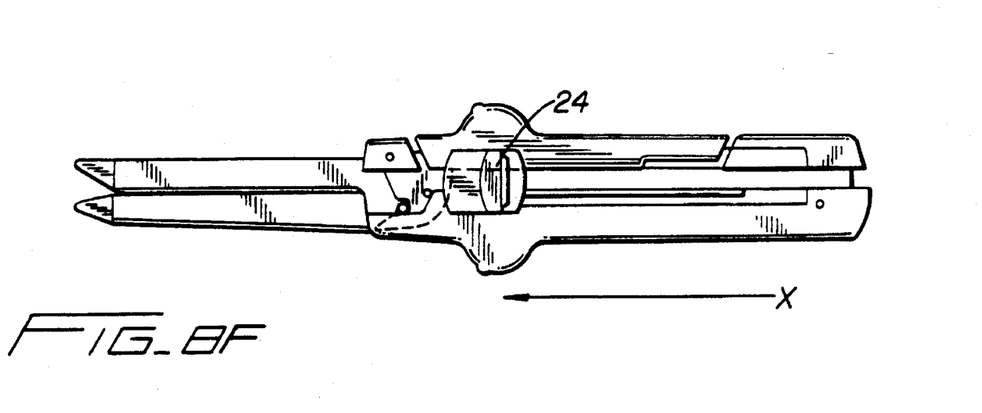

To fire the stapling device, the surgeon grasps the device in one hand with, for example his or her index finger on the front surface 47 of the finger grip 43 below the ridge 45 and with his or her middle finger on the front surface 53 of the finger grip 49 above the ridge 51. The actuator 24 is pushed leftwardly in the direction of arrow X, as shown in FIG. 8F, by the thumb of the surgeon's other hand engaged on the back surface 29 behind the ridge 27. This motion slides the actuating mechanism through the top beam, where the cam surfaces 124 on the left and right advancers 114 and 116 sequentially depress the staple drivers 76 to drive the staples 74 through the tissue clamped between the jaws toward the anvil surface 92. Simultaneously, the knife advancer 132 advances the cutting blade 128 between the slot 96 in the anvil surface 92 to cut the sutured tissue immediately after the tissue has been stapled. More particularly, as shown in FIG. 2, the length of the knife advancer 132 is less than that of the right and left advancers 116 and 114. With this arrangement, the cutting blade 128 lags behind the cam surfaces 124 and does not cut the tissue until it has been sutured. Because the cutting blade 128 is angled upwardly and backwardly as shown in the figures, the blade tends to move downwardly and the blade advancer tends to flex downwardly as tissue is encountered by the blade. Further this downward blade movement is guided by the floor below the slot 96 in the anvil which, as noted, slopes downwardly toward the nose 100. Thus a fresh blade cutting surface is maintained on the tissue. This feature allows for cleaner cutting of the tissue.

As will be appreciated, when the actuator 20 is in the ready-to-fire position shown in FIG. 8E, the lower coupling finger 152 on the actuator 24 is aligned with entry way 154 to the channel 38 in the bottom housing, and the upper coupling finger 150 is aligned with the entrance 156 of the groove 46 in the clamp housing 40. When the actuator is fired, the lower coupling finger 152 becomes engaged in channel 38. Similarly, the upper coupling finger 150 becomes engaged in groove 46 in the clamp housing 40. This interengagement prevents the upper and lower jaw members from being separated and the clamp housing and bar from being opened, thereby to protect the stapling instrument operator and the patient from unwanted exposure to the cutting blade.

Figure 8G:
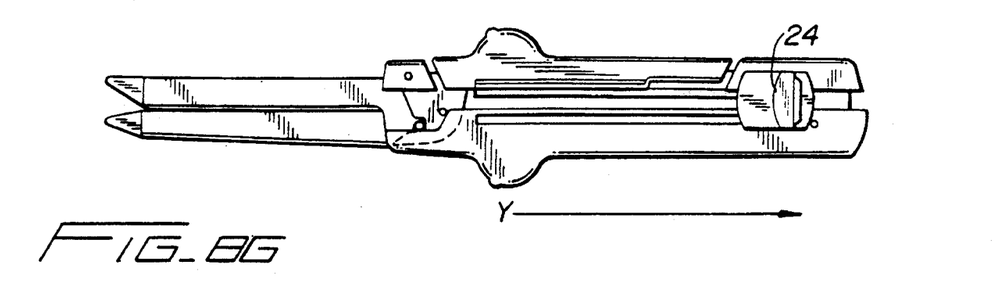
Figure 8H:
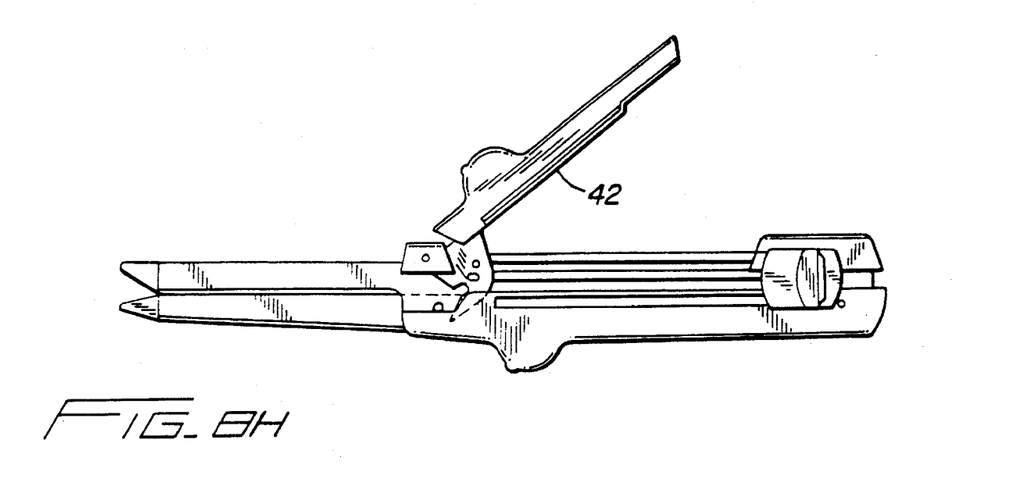
Figure 8I:
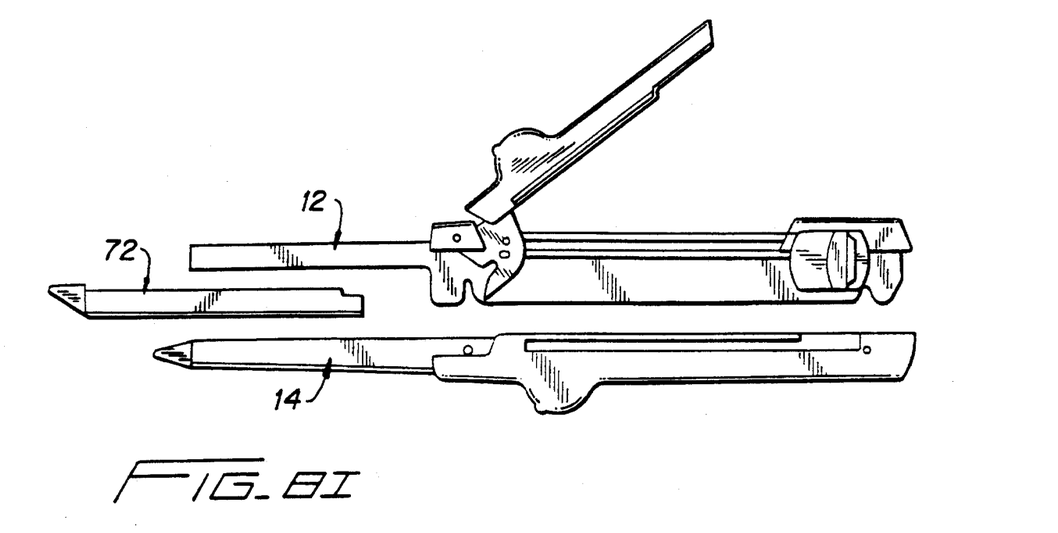

To release the jaw members from the sutured tissue, the actuator 24 is slid in the direction of the arrow Y in FIG. 8G and the clamp bar 42 is lifted as shown in FIG. 8H. When the jaw members are separated, the safety spring 86, which has been tripped extends to its fully deployed position as shown in FIG. 7, making it impossible to reclose the jaw members. The spent staple cartridge may then be removed as shown in FIG. 8I, and replaced with a loaded cartridge having a retracted safety spring so that the stapling device is made ready to be used again.

Accordingly, it will be readily understood that the present invention has many aspects and features that provide significant improvements over known linear surgical stapling instruments.

Although specific embodiments of the present invention have been described above in detail, it will be understood that this description is merely for purposes of illustration. Various modifications of and equivalent structures corresponding to the disclosed aspects of the preferred embodiments in addition to those described above may be made by those skilled in the art without departing from the spirit of the present invention which is defined in the following claims, the scope of which is to be accorded the broadest interpretation so as to encompass such modifications and equivalent structures.

What is claimed is:

1. An apparatus for applying surgical staples to body tissue comprising:

a) a cartridge assembly containing a plurality of surgical staples;

b) an anvil having a plurality of staple deforming pockets defined therein, the anvil and cartridge assembly being relatively movable between a first spaced apart position and a second position in close cooperative alignment with one another;

c) an actuation mechanism configured to advance through the cartridge assembly to sequentially eject the plurality of staples from the cartridge assembly to be driven against the anvil and deformed within the pockets;

d) a cutting blade support member supporting a cutting blade operatively associated with the actuation mechanism and configured to advance through the cartridge assembly in conjunction with the actuation mechanism; and e) a blocking member for preventing movement of the cartridge assembly and the anvil into close cooperative alignment after the plurality of staples have been ejected from the cartridge assembly, the blocking member mounted for deployment into a blocking position in response to the cutting blade support member moving toward and contacting the blocking member as the cutting blade support member advances through the cartridge assembly.

2. An apparatus as recited in claim 1, wherein the blocking member comprises a safety spring mounted in the cartridge assembly.

3. An apparatus as recited in claim 2, further comprising securing means for maintaining the safety spring in a non-blocking position prior to advancement of the cutting blade support member.

4. An apparatus as recited in claim 3, wherein the safety spring is releasable from the securing means upon advancement of the cutting blade support member and is movable into the blocking position when the cartridge assembly and the anvil are moved from the second position subsequent to the fasteners having been ejected from the cartridge.

5. An apparatus as recited in claim 4, wherein the safety spring includes a visible flag deployable upon movement of the safety spring into the blocking position.

6. An apparatus as recited in claim 4, wherein the cutting blade support member includes a trip structure for engaging the safety spring to release the safety spring from the securing means.

7. An apparatus as recited in claim 4, wherein the securing means includes a latch member having projecting ridges thereon for releasably securing the safety spring in a non-blocking position.

8. An apparatus as recited in claim 2, wherein the safety spring includes a central loop portion and first and second depending leg portions.

9. An apparatus as recited in claim 1, wherein the cartridge assembly is configured as a removable and replaceable unit.

10. An apparatus as recited in claim 9, wherein the blocking member is configured to move from the blocking position upon removal of a spent cartridge assembly and replacement with a loaded cartridge assembly.

* * * * *